United States Patent [19]

Nemec et al.

[11] 4,145,559
[45] Mar. 20, 1979

[54] ESTERS OF 4-SUBSTITUTED 2-METHYLENEGLUTARIC ACIDS AND METHOD FOR PREPARING SAME

[75] Inventors: Joseph W. Nemec; Richard B. Wuchter, both of Rydal, Pa.

[73] Assignee: Rohm and Haas Company, Philadelphia, Pa.

[21] Appl. No.: 521,215

[22] Filed: Nov. 6, 1974

Related U.S. Application Data

[63] Continuation-in-part of Ser. No. 863,690, Oct. 3, 1969, abandoned.

[51] Int. Cl.$^2$ ............................................. C07C 69/52
[52] U.S. Cl. ...................................... 560/190; 560/81; 560/139; 560/146; 560/171; 560/181; 560/193; 560/194; 560/196
[58] Field of Search .................... 260/485 R; 560/190, 560/193, 194, 196, 139, 146

[56] References Cited

U.S. PATENT DOCUMENTS

| 3,444,238 | 5/1969 | Weiss et al. | 260/485 |
| 3,484,475 | 12/1969 | Cornforth et al. | 260/485 |

FOREIGN PATENT DOCUMENTS 7142888  12/1971  Japan ...................................... 560/190

OTHER PUBLICATIONS

Fuson – Advanced Organic Chemistry, p. 84, John Wiley & Sons, Inc., New York, (1950).
Feit et al., Eur. Polym. J., 1971, 7(10), 1435–1443, (1971), (Ca–76, 86172m).

Primary Examiner—Jane S. Myers
Attorney, Agent, or Firm—Jordan J. Driks

[57] ABSTRACT

Esters of 4-substituted 2-methyleneglutaric acids are prepared by reacting an ester of acrylic acid with an ester of an α-substituted acrylic acid, such as an ester of methacrylic acid, in the presence of a tertiary organic phosphine, an organic phosphorus triamide, an organic phosphonous diamide, or an organic phosphinous amide.

8 Claims, No Drawings

ESTERS OF 4-SUBSTITUTED 2-METHYLENEGLUTARIC ACIDS AND METHOD FOR PREPARING SAME

CROSS-REFERENCE TO RELATED APPLICATION

This application is a continuation-in-part of our co-pending application Ser. No. 863,690, filed on Oct. 3, 1969, now abandoned.

This invention relates to certain new and useful 4-substituted 2-methyleneglutaric acid esters and to a method of preparing these esters.

The prior art methods of preparing 2-methyleneglutaric acid esters generally involve the dimerization and trimerization of acrylic acid esters, using various types of catalysts. In Rauhut et al. U.S. Pat. No. 3,074,999, Jan. 22, 1963, the use of tertiary organic phosphines as catalysts for the dimerization of acrylates is disclosed, and in Nemec et al. U.S. Pat. Nos. 3,342,853 and 3,342,854, Sept. 19, 1967, the use of organic phosphorus triamides, phosphonous diamides, and phosphinous amides as catalysts for the dimerization and trimerization of acrylates is disclosed. However, it was found that under the reaction conditions described in the above patents, esters of α-substituted acrylic acids, such as esters of methacrylic acid, do not dimerize. Thus, the scope of the class of 2-methyleneglutaric acid esters which may be produced by the prior art methods is quite limited. It has now been unexpectedly found that an acrylate and an α-substituted acrylate can be made to react to give a new class of 2-methylenglutaric acid esters.

According to the invention, a 4-substituted 2-methyleneglutaric acid ester of the formula

wherein R and R' are the same or different and may be alkyl groups of 1 to 18 carbon atoms, preferably of 1 to 8 carbon atoms, aryl groups of 6 to 10 carbon atoms, aralkyl groups of 7 to 12 carbon atoms, or dialkylaminoalkyl groups of 3 to 10 carbon atoms and R" is an alkyl group of 1 to 8 carbon atoms, an aralkyl group of 7 to 10 carbon atoms, an aryl group of 6 to 10 carbon atoms, a dialkylaminoalkyl group of 3 to 10 carbon atoms, or a haloalkyl group of 1 to 8 carbon atoms,
can be prepared by contacting a compound of the formula

wherein R is as defined above, with a compound of the formula

wherein R' and R" are as defined above, in the presence of a catalytic amount of a tertiary organic phosphine, an organic phosphorus triamide, an organic phosphonous diamide, or an organic phosphinous amide. In a preferred embodiment of the invention, R" is a methyl group, and R and R' are not identical groups.

Among the groups which R and R' can represent are methyl, ethyl, propyl, butyl, hexyl, octyl, decyl, dodecyl, tetradecyl, and octadecyl, in both straight and branched chain spatial configurations, as well as phenyl, benzyl, 2-phenylethyl, tolyl, dimethylaminomethyl, dimethylaminoethyl, diethylaminoethyl, diethylaminopropyl, and the like. The alkyl, aryl, and aralkyl groups represented by R and R' can also have as substituents groups such as halogen, alkyl, and alkoxy which will be inert to the process of the invention. Among the groups which R" can represent are methyl, ethyl, propyl, butyl, hexyl, and octyl, in both straight and branched chain spatial configurations, as well as dimethylaminoethyl, dimethylaminomethyl, diethylaminoethyl, dimethylaminopropyl, and the like. The alkyl groups represented by R" can also have as substituents groups such as halogen and alkoxy which will be inert to the process of the invention.

The tertiary organic phosphines which are useful as catalysts in the process of the invention generally have the formula

wherein Y in the above formula includes substituted and unsubstituted branched and straight chain, saturated and unsaturated alkyl groups, substituted and unsubstituted, saturated and unsaturated alicyclic groups, and substituted and unsubstituted aryl groups.

Typically, Y may represent substituted or unsubstituted methyl, ethyl, propyl, vinyl, allyl, butyl, hexyl, cyclopentyl, cyclohexyl, cyclohexenyl, octyl, dodecyl, octadecyl, phenyl, tolyl, benzyl, xylyl, and the like. Among the substituents which can be attached to the alkyl, alicyclic, or aryl groups are halogen, cyano, amino, hydroxyl, carbamyl, acyloxy, carbalkoxy, carboxy, alkyloxy, aryl, and aryloxy groups, and the like.

The mole ratio of the acrylate ester reactants to tertiary organic phosphine suitable for the present invention is generally greater than about 1:1, but there really is no lower limit other than that dictated by practicality. For example, a suitable but impractical ratio is 1:5 or lower, since the greater the amount of tertiary organic phosphine present the faster the reaction.

As to the upper concentration limit, it has been found that mole ratios above 200:1, acrylate reactants to tertiary organic phosphine, are less and less effective as the proportion increases. Preferably, concentrations in the range of 130:1 to 5:1 are employed.

Included among the tertiary organic phosphines suitable for the present invention are trimethylphosphine, trioctylphosphine, tributylphosphine, triisobutylphosphine, tricyclopentylphosphine, tricyclohexenylphosphine, triphenylphosphine, tris(cyanoethyl)phosphine, tris(2-carboxyethyl)phosphine, trivinylphosphine, tris(2-phenylethyl)phosphine, tris(2-butoxyethyl)phosphine, tris(trifluoroethyl)phosphine, and the like.

The organic phosphorus triamides which are useful as catalysts in the process of the invention generally have the formula

wherein Z and Z' can be the same or different.

Z and Z' represent alkyl groups of 1 to 18 carbon atoms joined to the nitrogen atoms at a primary carbon. It is preferred that these groups contain from 1 to 4 carbon atoms.

Z and Z' collectively with the nitrogen atom to which they are attached, may form a saturated cyclic amine group containing up to 5 carbon atoms in the ring, optionally containing 1 or more alkyl substituents having a total of up to 6 carbon atoms. This cyclic amine group may contain an oxygen atom or a sulfur atom, if desired.

Z and Z' as alkyl embodiments, may possess inert substituents as long as the carbon atom attached to the nitrogen is primary in structure. Such inert substituents include cyano, chloro, bromo, alkoxy or carbalkoxy moieties, among others. These are within the gamut of this invention. Neither Z nor Z' can be hydrogen or aryl.

Typically, Z and Z', individually, may be methyl, ethyl, propyl, butyl, pentyl, hexyl, octyl, dodecyl, octadecyl and, collectively with the nitrogen atom, may represent piperidino, morpholino, thiomorpholino, piperazino, pyrrolidinyl and ethylpiperidino.

Specific embodiments of the catalysts of Formula V typically include hexa-n-propylphosphorus triamide, hexaethylphosphorus triamide, hexa-n-butylphosphorus triamide, dimethyltetra-n-propylphosphorus triamide, tripiperidinophosphorus triamide, hexa-n-octylphosphorus triamide and hexamethylphosphorus triamide. Preferred embodiments are hexa-n-propylphosphorus triamide and hexa-n-butylphosphorus triamide.

The specific catalyst V as defined above, is employed in the present process in amounts as low as 0.25 mole percent but is preferably used in the range of about 0.7 to 1.5 mole percent. Greater amounts can be employed, if desired, but generally there is no advantage.

The catalyst can be employed as such or prepared in situ, as desired. If preparation in situ is contemplated, one employs phosphorus trichloride and the appropriate amine, as will be understood by those skilled in the art. The in situ preparation involves the formation of an amine hydrochloride salt as a by-product which must be substantially completely removed, such as by filtration or washing, as desired.

The organic phosphonous diamides and phosphinous amides which are useful as catalysts in the process of the invention generally have the following formulas, respectively

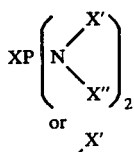  (VI)

or

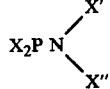  (VII)

In formulas VI and VII, X' and X'' may be the same or different, as desired. In formula VII, the X groups may be the same or different, as desired.

X' represents alkyl groups of 1 to 18 carbon atoms, preferably 1 to 4 carbon atoms, phenyl, or alkylsubstituted phenyl in which the alkyl substituent may be represented by one or more alkyl groups in which the total carbon content of the alkyl substitution ranges from 1 to 8 carbon atoms.

X' and X'' represent alkyl of 1 to 18 carbon atoms, preferably 1 to 4 carbon atoms. Furthermore, the X' and X'' groups, collectively with the nitrogen atom to which they are attached, may form a saturated cyclic amine group containing up to 5 carbon atoms in the ring and optionally containing one or more alkyl substituents having a total of up to 6 carbon atoms. This cyclic amine group may also contain an oxygen atom or a sulfur atom in the ring, if desired.

The X' and X'' groups as alkyl embodiments may possess inert substituents as long as the carbon atom attached to the nitrogen is primary in structure. Such inert substituents include cyano, chloro, bromo, alkoxy or carbalkoxy moieties, among others.

Typically, X may represent methyl, ethyl, propyl, butyl, pentyl, hexyl, octyl, dodecyl, octadecyl, phenyl, tolyl, xylyl, diethylphenyl and dibutylphenyl.

Typically, X' and X'', individually, may be methyl, ethyl, propyl, butyl, pentyl, hexyl, octyl, dodecyl, octadecyl, and the X' and X'' groups, collectively with the nitrogen atom to which they are attached, may represent piperidino, morpholino, thiomorpholino, piperazino, pyrrolidinyl, ethylpiperazino and diethylpiperazino.

Specific embodiments of the catalyst having formula VI typically include N,N,N',N'-tetramethyl-P-phenylphosphonous diamide, N,N,N',N'-tetra-n-butyl-P-phenylphosphonous diamide, N',N'-dioctyl-P-phenylphosphonous diamide, N,N,N',N'-tetra-n-butyl-P-ethylphenylphosphonous diamide, N,N,N',N'-tetramethyl-P-tolylphosphonous diamide, N,N,-diethyl-N',N'-di-n-butyl-P-octylphenylphosphonous diamide, phenyldipiperidylphosphine and tolyldimorpholino phosphine.

Specific embodiments of the catalyst having the Formula VII include N,N-dimethyl-P,P-diphenylphosphinous amide, N,N-diethyl-P,P-diethylphosphinous amide, N,N-di-n-butyl-P,P-diphenylphosphinous amide, N,N-dioctyl-P,P-diphenylphosphinous amide, N-methyl-N-dodecyl-P,P-diphenylphosphinous amide, N,N-dimethyl-P,P-dioctylphenylphosphinous amide, piperazinodiphenyl phosphine and pyrrolidinylditolyl phosphine.

The specific catalyst VI, as defined above, is employed in the present preparation of glutaric esters in amounts as low as about 0.25 mole percent, but is preferably used in the range of about 0.7 to 1.5 mole percent, with respect to the acrylate reactants. Greater amounts can be employed, if desired, but generally there is no advantage. The specific catalyst VII, as defined above, is used in amounts of up to about 8 mole percent, preferably 3 to 5 mole percent, with respect to the acrylate reactants. Actually, the upper amount of catalyst used is dictated largely by the economics of the process.

The catalyst may be employed as such or prepared in situ, as desired. If preparation in situ is contemplated, one employs the X-dichlorophosphine or $X_2$-chlorophosphine, as the case may be, and the appropriate amine, as will be understood by those skilled in the art. If the phosphonous diamide is to be used, then 4 moles of the amine is employed per mole of the X-dichlorophosphine. If the phosphinous amide is to be used, there is employed 2 moles of the amine per mole of the $X_2$-chlorophosphine. In either instance, the in situ preparation involves the formation of an amine salt as a by-product which must be substantially completely removed, such as by filtration or washing, as desired.

The process of the invention can be carried out within a wide range of temperatures. Generally, a reaction temperature of about −10° C. to about +100° C. will be suitable. The preferred temperature range is about 40° C. to 80° C. The pressure is not critical and the reaction is generally performed at atmospheric pressure, although subatmospheric and superatmospheric pressures are suitable. If desired, a nitrogen or other inert atmosphere can be used, but is not required. However, in some instances, such as when low molecular weight phosphorus triamides are used as catalysts, an inert atmosphere may be advantageous.

A solvent is not required in the present process, although it is frequently desirable to employ an inert, volatile, organic solvent. Typically, solvents such as acetonitrile, hexane, benzene, toluene, and the like, can be used. Since the α-substituted acrylate esters do not dimerize, these reactants can be used in excess over that required to form the product of the present invention. The excess of the α-substituted acrylate component will serve as a solvent and will help to minimize the dimerization of the acrylate ester.

The reaction can be carried out by adding the reactant esters to the catalyst or the reverse, as desired. It is preferred to add the acrylate incrementally to the mixture of the α-substituted acrylate and the catalyst with or without a solvent, at a rate substantially consistent with the rate of reaction. The reaction is somewhat exothermic in nature and the incremental addition of the acrylate ester to the mixture of the α-substituted acrylate ester and catalyst can be regulated to moderate the heat of the exothermic reaction, particularly in large volume preparation. Other addition methods can be employed. For example, when a solvent is employed, the mixture of esters can be added to the solvent and catalyst. Since the α-substituted acrylate ester does not dimerize in the presence of the catalysts of the invention, the reaction is preferably carried out by adding the reactive acrylate ester to the mixture of excess α-substituted acrylate ester and catalyst.

The 2-methyleneglutaric acid esters can be separated from the reaction mixture by any of the known techniques. Generally, distillation will be used, during which unreacted starting reagents and solvents, if used, will be removed first. The 4-substituted 2-methyleneglutarate can then be separated from any acrylate dimer which may have formed during the reaction by fractional distillation.

The 4-substituted 2-methylene glutaric acid esters produced by the process of the invention are useful as monomers, in forming both homopolymers and copolymers, and as chemical intermediates, especially in preparing the saturated analogues of these esters.

An advantage of the process of the present invention is that mixed esters of 4-substituted 2-methyleneglutaric acids can be prepared. By mixed esters are meant those compounds of Formula I in which R and R' represent different groups. For example, by using as the starting acrylate reagents ethyl acrylate and methyl methacrylate, a mixed ethyl-methyl ester can be obtained (that is, with R in Formula I being ethyl and R' being methyl). Similarly, by varying the starting acrylate and α-substituted acrylate, various other mixed esters can be prepared. The mixed esters and their saturated analogues, which can be prepared by hydrogenation of the 4-substituted 2-methyleneglutaric acid esters of the invention, would be extremely difficult to obtain except in complicated mixtures by any known procedure.

Hydrogenation of the 4-substituted 2-methyleneglutaric esters to their 2-methyl analogues can be accomplished by any of the various well-known processes. For example, hydrogenation can be carried out by dissolving the ester in a convenient organic solvent, adding a metallic catalyst, such as platinum, palladium, or Raney nickel, and introducing hydrogen gas into the solution.

The following examples will further illustrate this invention but are not intended to limit it in any way.

EXAMPLE 1

Preparation of 2-ethylhexyl 2-methylene-4-carbomethoxypentanoate

Phosphorus trichloride (6.85 g.) is added dropwise and continuously to a stirred solution containing 30.4 g. of di-n-propylamine dissolved in 100 ml. of hexane at 10° C. After complete addition, the reaction mixture is allowed to stir 1 hour at room temperature. Sufficient water (75 ml.) is then added to dissolve the amine salt formed, and the organic layer is separated. The organic layer is washed once with 75 ml. of water. Methyl methacrylate (1000 g.) and 2 g. of the methyl ether of hydroquinone are added to the organic layer and heated to 65° C. To this stirred solution, 276 g. of 2-ethylhexyl acrylate is added dropwise over 8 to 10 hours. After a total of 24 hours at 65° C., the hexane and unconverted esters are removed via distillation. The residue is distilled to give 200 g. of 2-ethylhexyl 2-methylene-4-carbomethoxypentanoate, b.p. 120°–125° C./0.1 mm, $n_D^{25}$ = 1.4452–1.4463 and 164 g. of di-2-ethylhexyl glutarate, b.p. 150°–155° C./0.1 mm, $n_D^{25}$ = 1.4513. The 2-ethylhexyl 2-methylene-4-carbomethoxypentanoate is saponified to give 2-methylene-4-methylglutaric acid having a melting point of 106° to 108° C. and an acid number of 727. This product is further identified by elemental analysis and nmr spectroscopy.

EXAMPLE 2

Preparation of ethyl 2-methylene-4-carbomethoxypentanoate

Ethyl acrylate (50 g.) is added dropwise under nitrogen to a solution maintained at 60° C. and containing 500 g. of methyl methacrylate, 2.0 g. of the methyl ether of hydroquinone, and 6.0 g. of hexa-n-propylphosphorus triamide. The reaction was held at 60° C. for a total of 24 hours. After removal of unrected ethyl acrylate and methyl methacrylate, the 69.2 g. of residue analyzes for 22.4 g. of ethyl 2-methylene-4-carbomethoxypentanoate and 27.8 g. of diethyl 2-methyleneglutarate. Spectral analysis is consistent for the structure of the products. Further, hydrolysis of the ethyl 2-methylene-4-carbomethoxypentanoate gives 2-methylene-4-methylglutaric acid, which was identical to that produced in Example 1.

EXAMPLE 3

Preparation of ethyl 2-methylene-4-carbomethoxypentanoate

Ethyl acrylate (50 g.) is added dropwise under nitrogen to a solution at 60° c. containing 500 g. methyl methacrylate, 1 g. of hydroquinone, and 10 ml. tributylphosphine. After remaining at 60° for about 24 hours, the excess methyl methacrylate and unconverted ethyl acrylate are removed at atmospheric pressure. The residue is distilled at 80°–90° C. and 1 mm. to give 33.8 g. of distillate which contains 70% of diethyl 2-methyleneglutarate and 30% of ethyl 2-methylene-4-carbomethoxypentanoate.

EXAMPLE 4

Preparation of N,N-dimethylaminoethyl 2-methyl-4-carbethoxy-4-pentenoate

Ethyl acrylate (50 g.) is added dropwise over 1½-2 hours to a stirred solution at 65° C. containing 785 g. of N,N-dimethylaminoethyl methacrylate, 2 g. of the methyl ether of hydroquinone, and 6.0 g. of hexa-n-propylphosphorus triamide. After stirring overnight at 65° C., the unconverted monomers are removed by distillation. From the residue there is obtained 33.6 g. of diethyl 2-methyleneglutarate and 7.1 g. of N,N-dimethylaminoethyl 2-methyl-4-carbethoxy-4-pentenoate, b.p. 92°–95° C./0.1 mm, $n_D^{25} = 1.4445$.

It is to be understood that changes and variations may be made without departing from the spirit and scope of the invention as defined by the appended claims.

We claim:

1. A process for the preparation of a compound of the formula

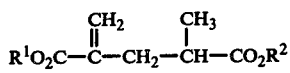

wherein $R^1$ and $R^2$ are individually alkyl groups of 1 to 18 carbon atoms, aryl groups of 6 to 10 carbon atoms, aralkyl groups of 7 to 12 carbon atoms, or dialkylaminoalkyl groups of 3 to 10 carbon atoms, which comprises contacting a compound of the formula $$CH_2=CH-CO_2R^1$$

wherein $R^1$ is as defined above, with a compound of the formula

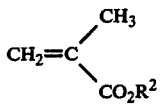

wherein $R^2$ is as defined above, in the presence of a catalytic amount of a tertiary organic phosphine, an organic phosphorus triamide, an organic phosphonous diamide, or an organic phosphinous amide as a catalyst.

2. A process according to claim 1 wherein the catalyst is hexa-n-propylphosphorus triamide.

3. A process according to claim 1 wherein the catalyst is tributylphosphine.

4. A process according to claim 1 which is carried out at a temperature of about $-10°$ C. to about $+100°$ C.

5. A process according to claim 1 wherein $R^1$ and $R^2$ are different.

6. A process according to claim 5 wherein $R^1$ is an ethyl group and $R^2$ is a methyl group.

7. A compound of the formula

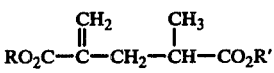

wherein R is a 2-ethylhexyl group and R' is a methyl group.

8. A compound of the formula

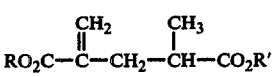

wherein R is an ethyl group and R' is a 2-(N,N-dimethylamino)ethyl group.

* * * * *